(12) United States Patent
Coppi

(10) Patent No.: US 9,539,414 B2
(45) Date of Patent: Jan. 10, 2017

(54) VARIABLE CURVATURE CATHETER

(71) Applicant: Gioachino Coppi, Modena (IT)

(72) Inventor: Gioachino Coppi, Modena (IT)

(*) Notice: Subject to any disclaimer, the term of this patent is extended or adjusted under 35 U.S.C. 154(b) by 0 days.

(21) Appl. No.: 14/760,579

(22) PCT Filed: Nov. 26, 2013

(86) PCT No.: PCT/IB2013/060411
§ 371 (c)(1),
(2) Date: Jul. 13, 2015

(87) PCT Pub. No.: WO2014/118605
PCT Pub. Date: Aug. 7, 2014

(65) Prior Publication Data
US 2015/0352328 A1     Dec. 10, 2015

(30) Foreign Application Priority Data
Jan. 30, 2013   (IT) .............................. PD2013A0020

(51) Int. Cl.
*A61M 25/00* (2006.01)
*A61M 25/01* (2006.01)

(52) U.S. Cl.
CPC ..... *A61M 25/0147* (2013.01); *A61M 25/0074* (2013.01); *A61M 2025/0079* (2013.01); *A61M 2025/015* (2013.01)

(58) Field of Classification Search
CPC .................... A61M 25/0147; A61M 25/0074; A61M 2025/015; A61M 2025/0079; A61M 25/0105; A61M 25/0161; A61M 2025/0163; A61B 2034/715; A61B 2017/003
See application file for complete search history.

(56) References Cited

U.S. PATENT DOCUMENTS

| 5,730,724 A | 3/1998 | Plishka et al. |
| 2009/0182268 A1* | 7/2009 | Thielen ............. A61M 25/0138 604/95.04 |

OTHER PUBLICATIONS

PCT International Search Report and the Written Opinion, Application No. PCT/IB2013/060411 filed Nov. 26, 2013, dated Apr. 16, 2014.

* cited by examiner

*Primary Examiner* — Katherine Rodjom
*Assistant Examiner* — Michael Mendoza
(74) *Attorney, Agent, or Firm* — MacMillan, Sobanski & Todd, LLC

(57) ABSTRACT

A variable curvature catheter (4) with a strong capacity to maintain the desired curvature comprising a catheter body (8) which extends from a proximal end (12) to a distal end (16), provided with a side wall (20) which defines at least one cavity (24); the catheter body (8) comprises, at said distal end (16), a variable curvature section (28) which ends in a tip (32). Inside the cavity (24) at least one traction wire (36) is housed having an ascending branch (40), which extends from the proximal end (12) towards the distal end (16) so as to at least partially go through the variable curvature section (28) at least as far as a first fork (44). The traction wire (36) extends from the first fork (44) at least partially going through the variable curvature section (28), coming out of the variable curvature section (28) and rejoining the ascending branch (40) at said first fork (44), so as to form a closed loop (48) which at least partially goes through the variable curvature section (28) closing itself on the first fork (44). The traction wire (36), after closing itself in a loop (48) on the first fork (44), extends towards the proximal end (12) along a descending branch (52). The descending branch (52) slides in relation to the ascending branch (40) inside constraint means (64, 68, 72) joined to the ascending branch (40) at said first fork (44), the constraint means (64, 68, 72) permitting the relative sliding of the descending branch (52) in relation to the ascending branch (40) and ensuring the closure of the loop (48) run through by the traction wire (36) along the variable curvature section (28). Applying the traction instead to the ascending wire (40) and releasing the descending wire (52), the curvature is loosened and it is possible to remove the wire completely, leaving the lumen (24) of the catheter free. The catheter (4) may comprise at least one guide element (92) of an elongated and flexible shape, slidingly engageable inside the cavity or lumen (24) of the catheter body (8), to come out through the tip (32) and a stabilization element (96) of an elongated shape along a main direction of extension (X-X) and flexible, slidingly engageable inside the cavity or lumen (24) of the catheter body (8) into which it is introduced and which it comes out of through a stabilization aperture (100).

17 Claims, 8 Drawing Sheets

VARIABLE CURVATURE CATHETER

Figure 1:
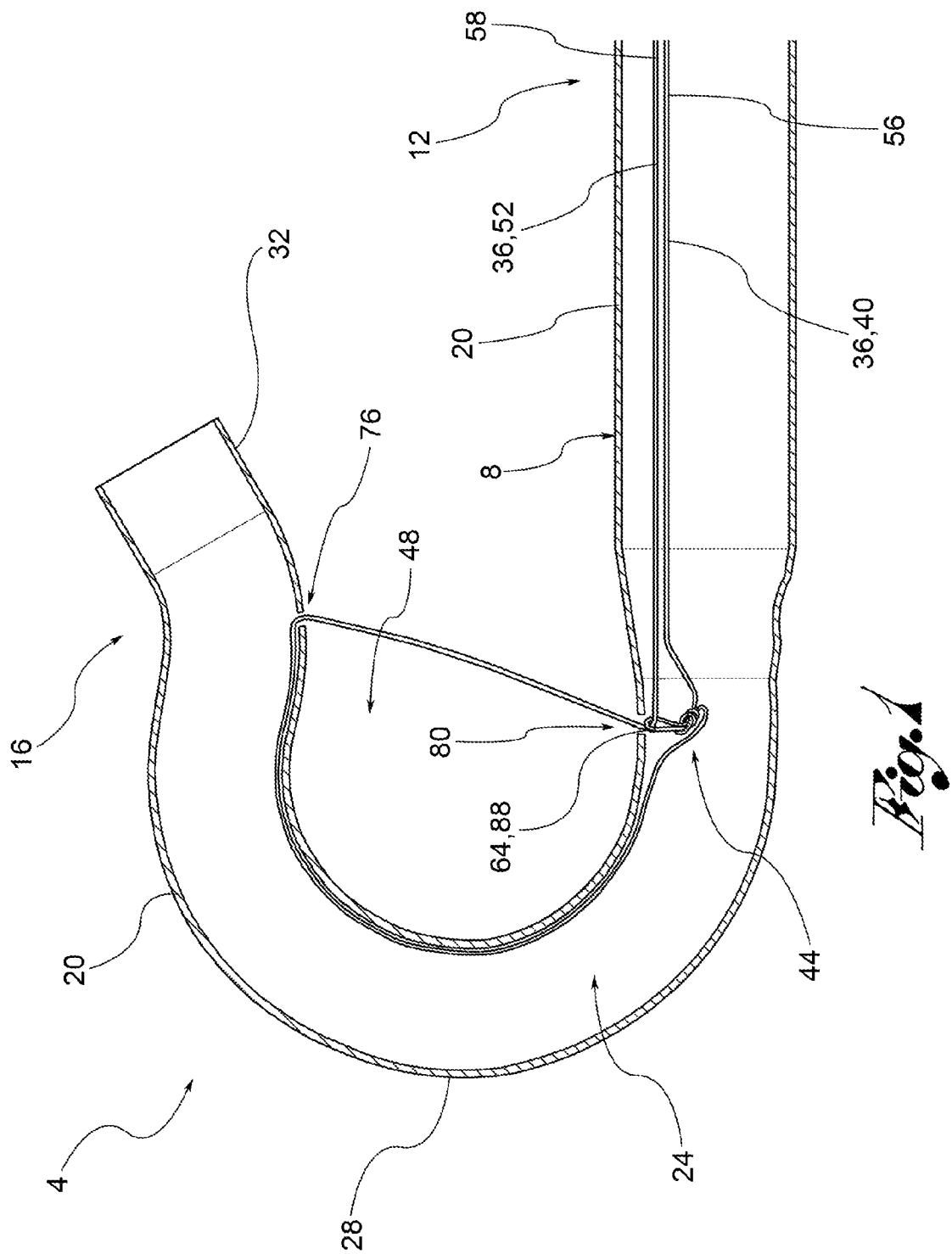
Figure 2:
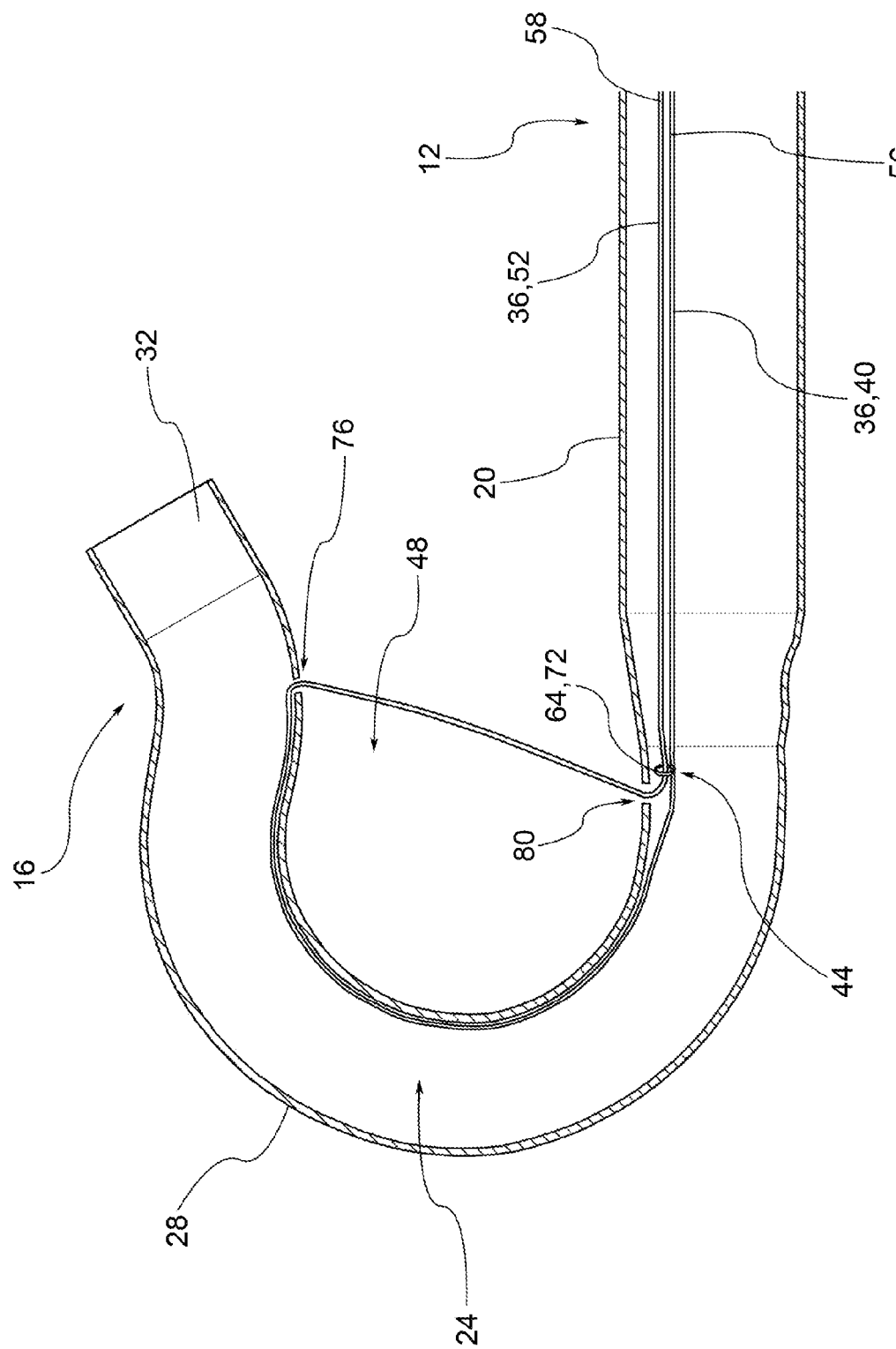
Figure 3:
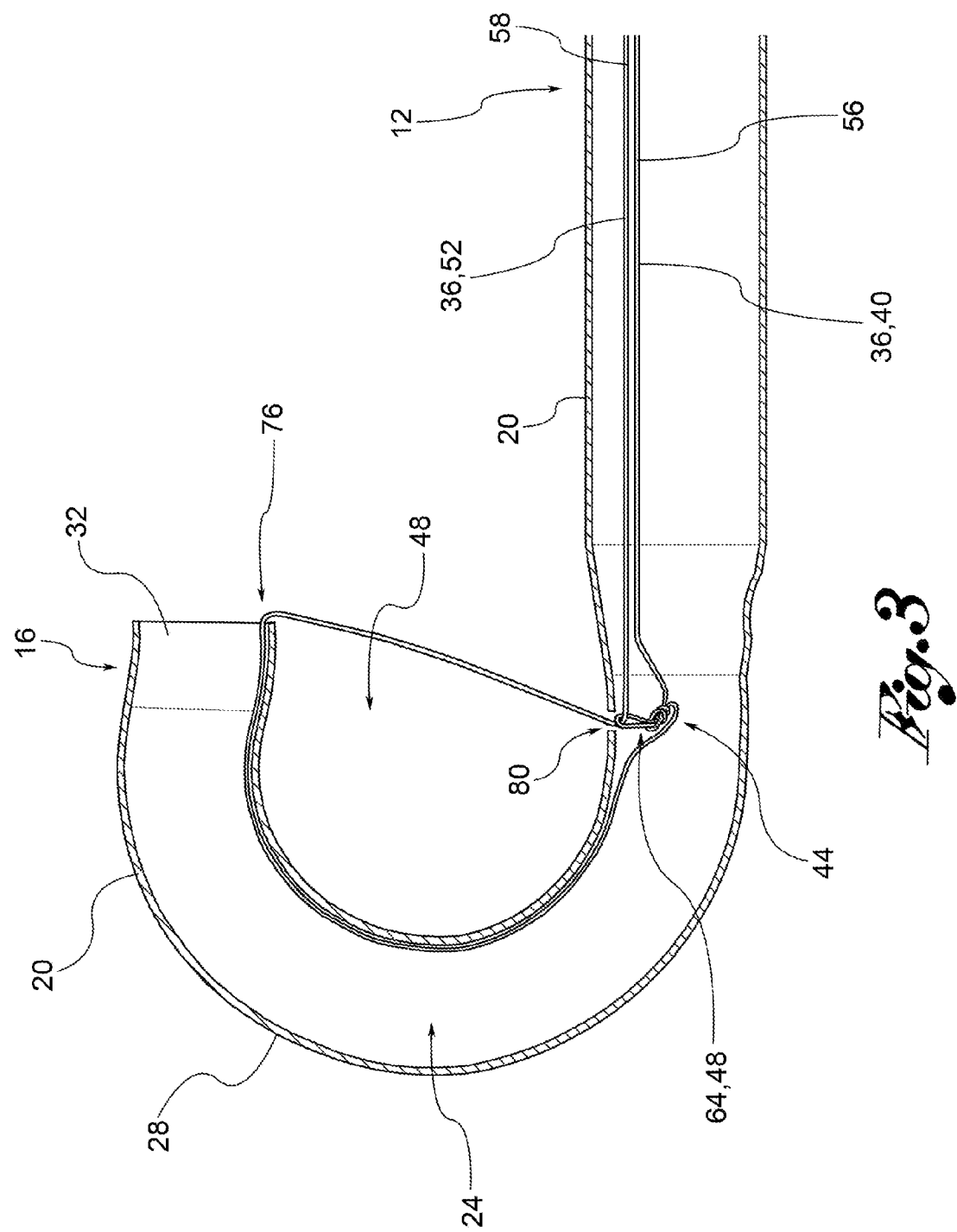
Figure 4:
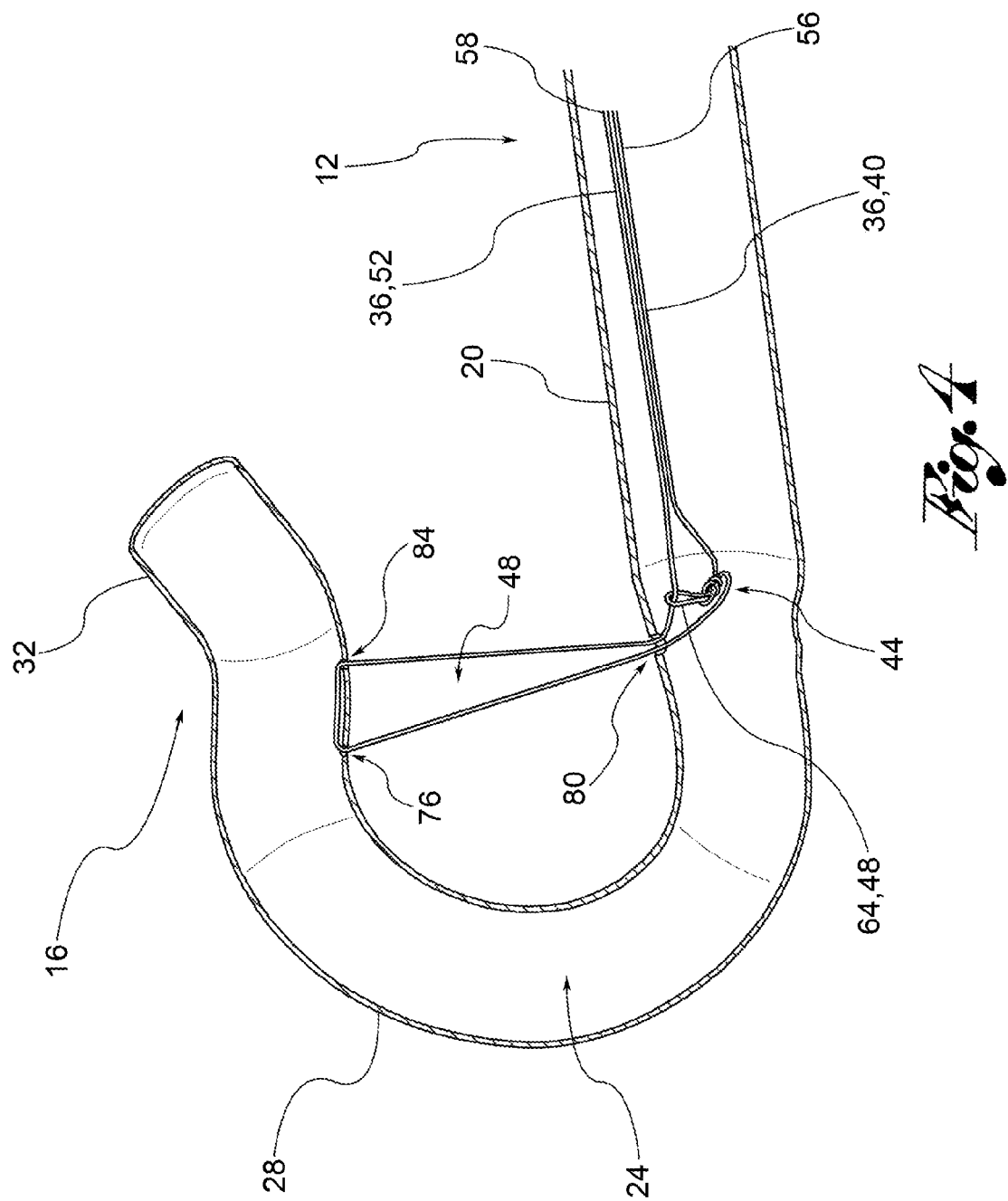
Figure 5:
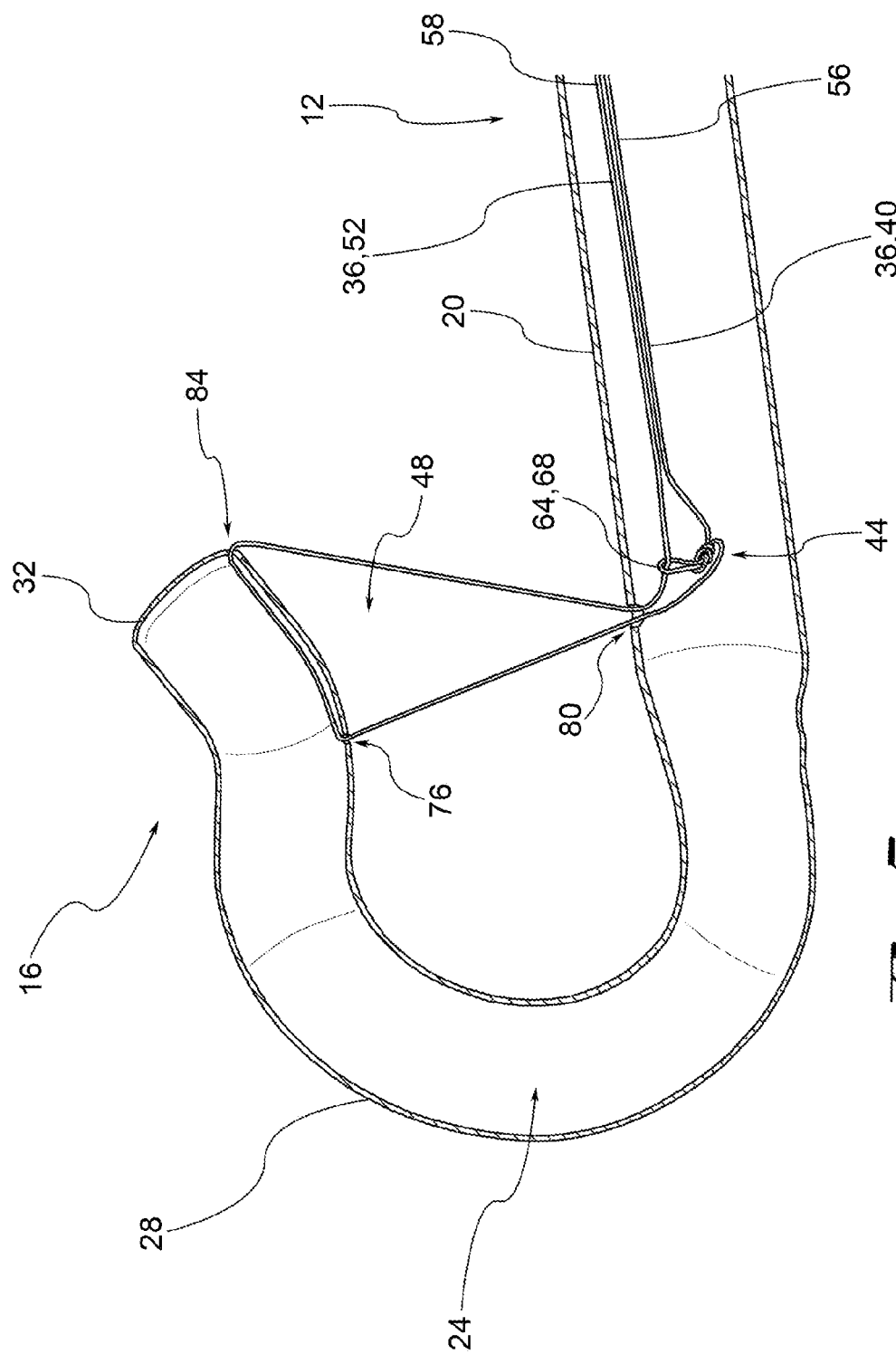
Figure 6:
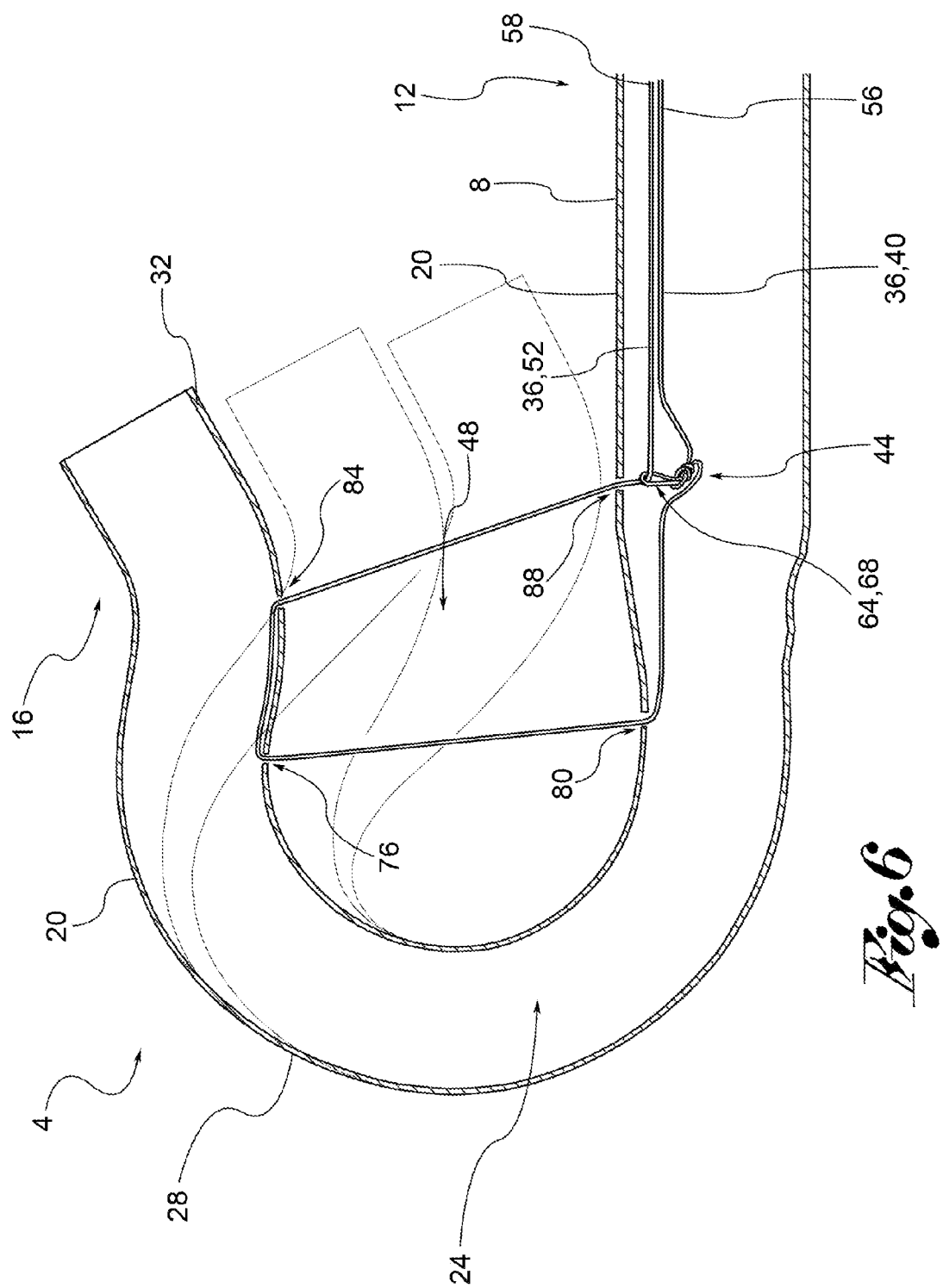
Figure 7:
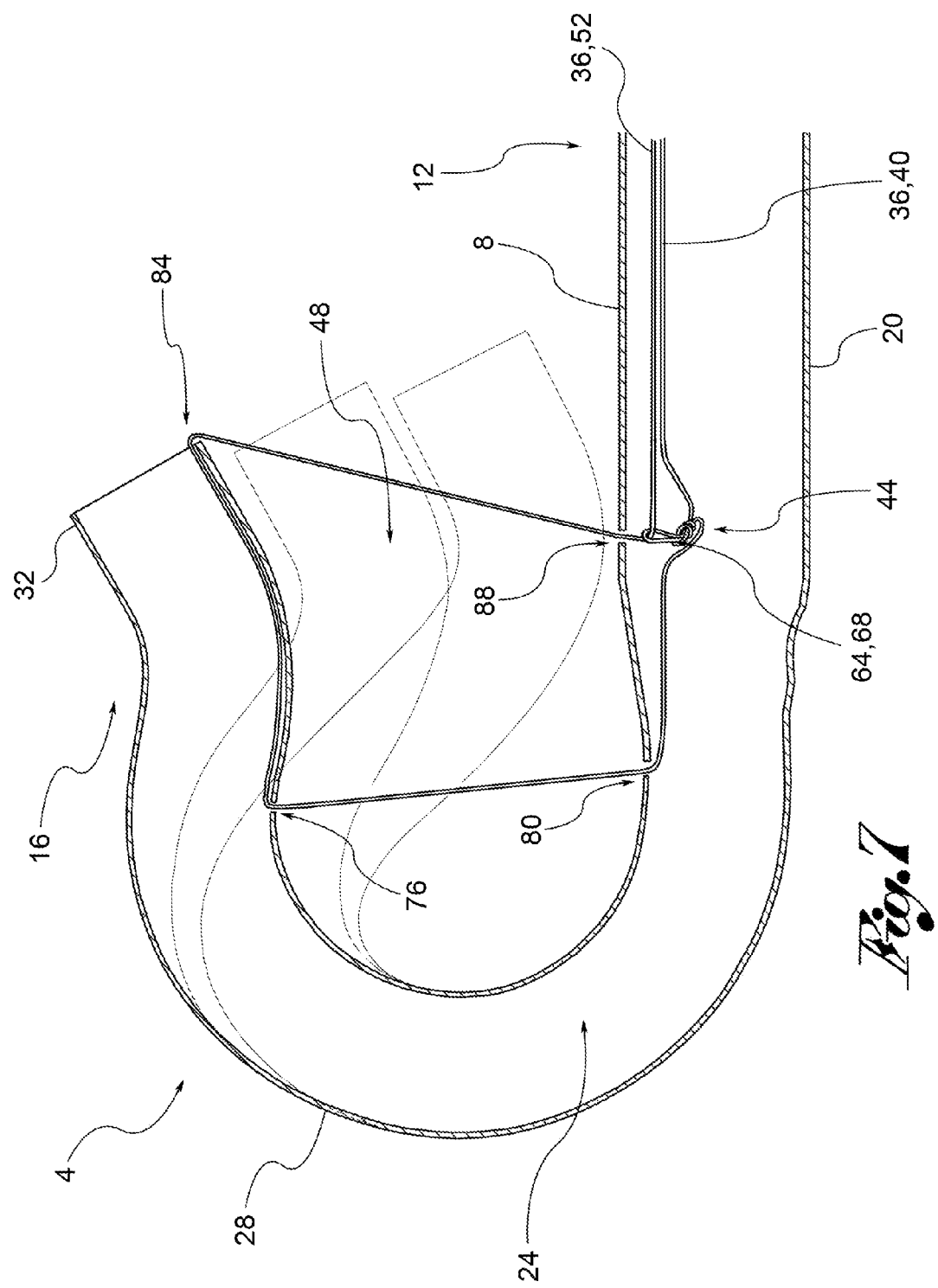

This is a national stage application filed under 35 U.S.C. §371 of international application PCT/IB2013/060411, filed under the authority of the Patent Cooperation Treaty on Nov. 26, 2013, published; which claims the benefit of Patent Application No. PD2013A000020, filed on Jan. 30, 2013. The entire disclosures of all the aforementioned applications are expressly incorporated herein by reference for all purposes.

The present invention relates to a catheter fitted with a variable curvature distal tip and a relative curvature method of a catheter.

In particular, as described further below, the present invention relates to a catheter fitted with a distal tip of variable curvature, even minimal, which can be accentuated as wished and stabilised against straightening forces.

In particular, it is known of in the art to make catheters having deformable and/or curvable distal tips, acting on the proximal end of the catheter, so as to facilitate the entrance of the catheter inside the vessels. These tips have the limitations both of a fixed geometry designed to engage angled vessels but also that of not sufficiently withstanding the straightening forces determined by objects which must follow a pre-ordained curvature, such as for example rigid guides or operating catheters which must run through such guides.

The solutions of the prior art are varied and often provide for complicated architectures of the catheters fitted with inner armours capable of deforming the tip of the catheter acting on the proximal end. In addition, the prior solutions do not permit accurate maintenance of the curvature of the catheter when it is subjected to straightening forces by stiff or superstiff guides or by catheters fitted on said guides and pushed beyond the apex of the variable curvature catheter for operating purposes (for example an angioplastic balloon or catheters carrying stents or stentgrafts).

The solutions of the prior art have further drawbacks.

In fact, on the one hand they require complex and expensive catheter geometries to be made and on the other, to modify and firmly maintain the curvature of the tip of the catheter they require the surgeon to operate with both hands, or in any case acting on two different commands. The prior solutions thus prove expensive to make and complicated to use.

The purpose of the present invention is to make a catheter which overcomes the drawbacks mentioned with reference to the prior art in a simple and economical manner.

Such drawbacks and limitations are resolved by a catheter according to claim 1

Other embodiments of the catheter according to the invention are described in the subsequent claims.

Further characteristics and advantages of the present invention will be more clearly comprehensible from the description given below of its preferred and non-limiting embodiments, wherein:

FIGS. 1-7 show cross-section views of catheters according to possible embodiments of the present invention.

The elements or parts of elements common to the embodiments described below will be indicated using the same reference numerals.

With reference to the aforementioned figures, reference numeral 4 (FIG. 1) globally denotes a medical variable curvature catheter comprising a catheter body 8 which extends from a proximal end 12 to a distal end 16, the catheter body 8 being provided with a side wall which defines at least one cavity or lumen 24.

For the purposes of the present invention the catheter may be of any shape, have any lumen, dimension and material depending on the type of specific application. In particular, the variable curvature catheter which the present invention relates to is suitable for angioplastic use in that it permits extremely precise and controlled modification of the distal curvature so as to be able to enter vessels without running the risk of dissections or other injury.

The catheter body 8 comprises, at said distal end 16, a variable curvature section 28 which ends in a tip 32.

Advantageously, inside the cavity or lumen 24 of the catheter body 8 at least one traction wire 36 is housed.

Said traction wire may be made of any material and will have a diameter such as to pass inside the cavity 24. The diameter of such wire, in particular, may be very fine and resistant so as to also permit the passage of guides and/or operating catheters. The traction wire 36 comprises an ascending branch 40 which extends from the proximal end 12 to the distal end 16, so as to at least partially go through the variable curvature section 28 at least as far as a first fork 44.

Preferably, the traction wire 36 extends from the first fork 44 at least partially going through the variable curvature section 28, coming out of the variable curvature section 28 and rejoining the ascending branch 40 at said first fork 44, so as to form a closed loop which at least partially goes through the variable curvature section 28 closing itself on the first fork 44. The definition of closed loop should be understood in its widest sense; in other words the definition of loop is not tied to a specific geometry, for example circular, but may be triangular, square and in general polygonal.

The traction wire 36, after closing itself in a loop on the first fork 44, extends towards the proximal end 12 of the catheter along a descending branch 52.

The ascending branch 40 and the descending branch 52 of the traction wire 36 respectively end with respective ends 56, 58 positioned on the proximal end 12 of the catheter 4 so as to permit their operation and pulling independently of each other, as described further below.

Advantageously the descending branch 52 slides in relation to the ascending branch 40 inside constraint means 56 joined to the ascending branch 40 at said first fork 44, said constraint means 64 permitting the relative sliding of the descending branch 52 in relation to the ascending branch 40 and ensuring the closure of the loop 48 run through by the traction wire 36 along the variable curvature section 28. This way the sliding of the descending branch 52 modifies the curvature of the catheter 4 at the variable curvature section 28. In particular, the sliding of the descending branch 52 towards the proximal end 12, that is to say the pulling of the end 58 of the descending branch 52, results in the closure of the loop 48 which tends to close the variable curvature section 28 inwardly.

In other words, by pulling the end 58 of the descending branch 52 the loop 48 is tightened and thus the variable curvature section 28 tends to close, assuming an increasingly smaller curvature radius. In addition, by pulling the end 58 of the descending branch 52 and keeping it taut, better resistance is provided to the straightening forces of any bodies pushed out by said catheter, such as rigid guides or operating catheters.

In addition, by pulling the end 56 of the ascending branch 40, and releasing the end 58 of the descending branch 52, the width of the loop 48 can instead be increased, which will tend to return to its original curvature and thus increase the curvature radius of the variable curvature section 28. In addition, by pulling the end 56 of the ascending branch 40 the traction wire can be fully extracted from the catheter body 8, leaving the lumen 24 of the catheter 4 entirely free. This option is useful for possible operating purposes requiring an entirely free lumen in the moment in which the guide catheter is in the desired position.

According to one embodiment, the constraint means 64 comprise a noose 68 made with said ascending branch 40. In other words, the noose 68 may be made by appropriately knotting the ascending branch 40 to form a micro noose.

According to a further embodiment, the constraint means 64 comprise a coupling element 72 closed in a loop so as to form a lumen for the passage and relative sliding of the descending branch 52.

According to a possible embodiment (FIGS. 1-2) at least a portion of the traction wire 36, constituting the closed loop 48 passes through the variable curvature section 28 of the catheter 4 internally, following the curvature inside the cavity 24, so as to come out of a first distal hole 76 made on the side wall 20 at the distal end 16 and to go back into the catheter 4 through a first proximal hole 80 made in the side wall 20 and facing the first fork 44, so as to subtend the arch formed by the variable curvature section 28.

According to a further embodiment (FIG. 3) at least a portion of the traction wire 36, constituting the closed loop 48 passes through the variable curvature section 28 of the catheter 4 internally, following the curvature inside the cavity 24, so as to come out of a first distal hole 76 made on the tip 32 (or from the tip itself) of the distal end 16 and to go back into the catheter 4 through a first proximal hole 80 made in the side wall 20 and facing said first fork 44, so as to subtend the arch formed by the variable curvature section 28.

According to a further embodiment (FIG. 4) the ascending branch 40 goes through at least a first proximal hole 80 in the side wall 20, positioned near said first fork 44, so as to come out of the catheter 4, subtending the variable curvature section 28, go back into the catheter 4 through a first distal hole 76 made in the side wall 20, run through the variable curvature section 28 at least partially, come out through a second distal hole 84 made in the side wall 20, and go back into the catheter 4 through the first proximal hole 80 and close itself in a loop on the first fork 44 passing through the constraint means 64,68,72.

According to a further variant (FIG. 5) the second distal hole 84 is positioned on the tip 32 (or the tip is used for the exit of the wire) of the distal end 16 of the catheter 4.

Preferably, the first proximal hole 80 is of such breadth as to prevent the crossing or transit of the constraint means 64, 68, 72 joined to the ascending branch 40.

According to a further embodiment (FIG. 6) the ascending branch 40 goes through at least a first proximal hole 80 in the side wall 20, so as to subtend the variable curvature portion 28, go back into the catheter 4 through a first distal hole 76 made in the side wall 20, run through the variable curvature section 28 at least partially, come out through a second distal hole 84 made in the side wall 20, go back into the catheter 4 through a second proximal hole 88, different from the first proximal hole 80, and close itself in a loop on the first fork 44 passing through the constraint means 64,68,72.

According to a further variant (FIG. 7), the second distal hole 84 is positioned on the tip 32 (or is constituted by said tip) of the distal end 16 of the catheter 4.

Preferably, the first and the second proximal holes 80, 88 are of such breadth as to prevent the crossing or transit of the constraint means 64, 68, 72 joined to the ascending branch 40.

Preferably, the catheter 4, at said proximal end 12, comprises traction means (not shown) of said ends 56, 58 which permit an independent and/or contemporaneous operation thereof so as to modify the curvature of the variable curvature section 28. For example, said traction means of the wire may be attached to the catheter or also be of the type detachable from the catheter.

According to one embodiment of the present invention, the catheter 4 comprises at least one guide element 92 of an elongated and flexible shape, slidingly engageable inside the catheter body 8, that is to say inside the cavity or lumen 24, to come out through the tip 32 which acts as a directing element of said catheter. The guide element 92 thus constitutes a guide for said catheter so as to sustain it during the ascent of the vessels inside which the catheter is inserted.

In addition, according to one embodiment, the catheter 4 comprises a stabilisation element 96 of an elongated shape, preferably threadlike and flexible, slidingly engageable inside the cavity or lumen 24 of the catheter body 8 into which it is introduced and which it comes out of through a stabilisation aperture 100 placed at the distal end 16 of the catheter body 8.

Both the stabilisation element 96 and the guide element 92 are housed in the same lumen or cavity 24.

Figure 8:
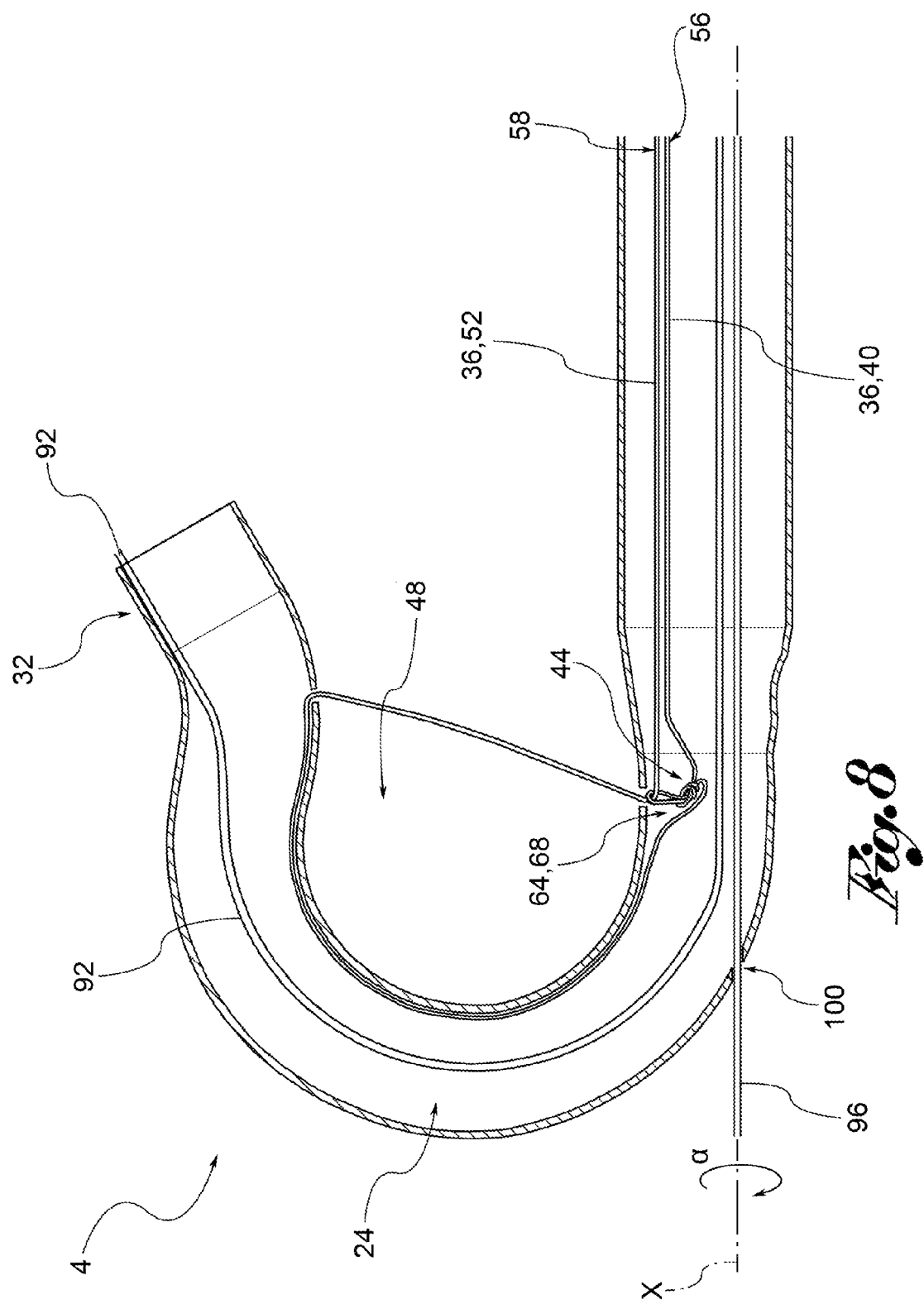

In particular, the stabilisation element 96 has an elongated shape along a main direction of extension X-X, substantially parallel to the extension of the catheter body 8. As said, the stabilisation element 96 comes out of the catheter body 8 through the stabilisation aperture 100: thus the entire catheter may be rotated around the stabilisation element 96, that is to say around the main direction of extension X-X, pivoting on said stabilisation element. Such rotation a (FIG. 8) makes it possible to enter the vessels more easily. The rotation of the catheter 4 around the stabilisation element 96 may be performed by acting on the guide element itself which is free to move, and to be rotated, inside said cavity 24. It is to be noted that, the stabilisation element 96 may also be fully retracted inside the cavity 24 so as not to project through the stabilisation aperture 100 and to be used, together with the guide element 92, to guide the ascent of the catheter inside the chosen vessel. In the same way both the stabilisation element 96 and the guide element 92 may be continually advanced/retracted for all the ascent and/or extraction operations of the vessel or vessels progressively entered. Should one wish to use the stabilisation guide as a pivot for the tip, it should be fitted to the catheter by extracting it and making the stabilisation guide pass backwards from the hole at the dorsal base of the curvature (see dual guide catheter). In addition, both the stabilisation element 96 and the guide element 92 may be fully extracted from the catheter so as to completely free the lumen 24.

In addition, the traction wire can come out, that is be extracted from the bottom of the catheter or from one side possibly with an arm also fitted with a valve.

Preferably, the guide element 92 and the stabilisation element 96 can act in conjunction with the traction wire 36 so as to control with extreme precision the exact curvature of the distal end 16 of the catheter 4. In fact, while on the one hand the guide element 92 and the stabilisation element 96 tend to straighten the distal end or tip of the catheter, on the other, operating appropriately on the ends 56, 58 respectively of the ascending branch 40 and of the descending branch 52, it is possible to counter such straightening and firmly maintain the exact curvature imposed by the surgeon during the operation. In any case it will always be possible to completely free the lumen 24 by individually or independently extracting the traction wire and/or stabilisation element 96 and/or guide element 92 depending on the specific and contingent requirements of the surgeon.

The functioning of a catheter according to the invention will now be described.

Starting from a catheter as mentioned above (preferably but not exclusively a guide catheter with Multipurpose type slight distal curve or with a preformed curve as per drawings), the curvature of the variable curvature section 28 may be modified by simply acting on the ends 56,58 from the side of the proximal end 12 of the catheter body 8.

In fact, by pulling the end 58 of the descending branch 52, said descending branch tends to close the loop 48 and thus close the variable curvature section 28. Such narrowing of the loop takes place thanks to the fact that the constraint means prevent the ascending branch from ascending and coming out of the variable curvature section.

In other words, the constraint means form a kind of noose, which can be closed by pulling the end 58 of the descending branch 52 and may be opened, up to the complete extraction of the traction wire 36, by pulling the end 56 of the ascending branch. When the end 58 is simply released, accompanied possibly by a slight pulling of the end 56 of the ascending branch 40, the catheter will tend to return to its original position. By keeping the end 58 of the descending branch 52, taut rather, the catheter will tend to maintain the desired curvature posing great resistance to the straightening forces of the catheter itself. Such straightening forces may even be of considerable strength, due for example to the passage of instruments with a "great straightening force" such as stents and stengrafts.

As described above, the functioning of the traction wire, and thus the possibility of controlling the exact curvature of the tip 32 of the catheter 4, increasing or reducing the curvature radius by appropriate pulling on the ends 56, 58 of the ascending 40 and descending branch 52, acts in conjunction with the guide element 92 and with the stabilisation element 96. In fact, said guide element 92 and the stabilisation element 96 make it possible to support the curvature of the catheter at all times, and even to rotate said catheter, with the additional possibility of controlling the curvature imposed on each occasion depending on the surgeon's requirements, at all times and with extreme precision, and also keeping such curvature blocked.

As may be appreciated from the description, the catheter according to the invention makes it possible to overcome the drawbacks presented in the prior art.

In particular the catheter is easy to manufacture in that it is sufficient to provide the holes, made on the side wall of the catheter, for the insertion and exit of the traction wire, and the traction wire itself. The present invention may thus also be applied to prior solutions of catheter, by simply adding the traction wire and the relative entrance and exit holes.

In addition, the catheter according to the invention is easy to use given that it is possible for the surgeon to modify the curvature acting on a single end of said wire, that is the end of the descending branch, to increase the curvature: the surgeon can thus modify the curvature of the distal end of the catheter with one hand and with extreme precision even making it functional to the passage of instruments with a great straightening force such as stents and stengrafts.

In addition, the traction wire may be easily removed from the catheter again acting on the proximal end and again with one hand only: it is sufficient, as seen, to pull the end of the ascending branch of the traction wire so as to be able to completely extract said wire from the catheter.

This operation is extremely useful at the moment in which, after modifying the tip of the catheter as required and having then entered the chosen vessel, the complete removal of the traction wire offers the advantage of being able to recover the entire inner lumen of the catheter for the passage of subsequent surgical instruments without running the risk that these may get tangled with or in any case interfere with said traction wire.

A person skilled in the art may make numerous modifications and variations to the catheters described above so as to satisfy contingent and specific requirements, while remaining within the sphere of protection of the invention as defined by the following claims.

The invention claimed is:

1. Variable curvature catheter comprising
a catheter body which extends from a proximal end to a distal end, the catheter body being fitted with a side wall which defines at least one cavity,
the catheter body comprising, at said distal end, a variable curvature section which ends in a tip,
wherein inside the cavity of the catheter body at least one traction wire is housed having an ascending branch, which extends from the proximal end towards the distal end so as to at least partially go through the variable curvature section at least as far as a first fork,
the traction wire extends from the first fork at least partially going through the variable curvature section, coming out of the variable curvature section and rejoining the ascending branch at said first fork, so as to form a closed loop which at least partially goes through, the variable curvature section closing itself on the first fork,
wherein the traction wire, after closing itself in a loop on the first fork, extends towards the proximal end along a descending branch,
wherein the descending branch slides in relation to the ascending branch inside a constraint joined to the ascending branch at said first fork, said constraint permitting the relative sliding of the descending branch in relation to the ascending branch and ensuring the closure of the loop run through by the traction wire along the variable curvature section, the sliding of the descending branch modifying the curvature of the distal portion of the catheter.

2. Catheter according to claim 1, wherein said constraint comprises a noose made with said ascending branch.

3. Catheter according to claim 1, wherein said constraint comprises a coupling element closed in a loop so as to form a lumen for the passage and relative sliding of the descending branch.

4. Catheter according to claim 1, wherein at least a portion of the traction wire, constituting the closed loop passes through the variable curvature section of the catheter internally, following the curvature inside the cavity, so as to come out of a first distal hole made on the side wall at the distal end and to go back into the catheter through a first proximal hole made in the side wall and facing said first fork, so as to subtend the arch formed by the variable curvature section.

5. Catheter according to claim 1, wherein at least a portion of the traction wire, constituting the closed loop passes through the variable curvature section of the catheter internally, following the curvature inside the cavity, so as to come out of a first distal hole made on the tip of the distal end and to go back into the catheter through a first proximal hole made in the side wall and facing said first fork, so as to subtend the arch, formed by the variable curvature section.

6. Catheter according claim 1, wherein the ascending branch goes through at least a first proximal hole in the side wall, positioned near said first fork, so as to come out of the catheter, subtending the variable curvature section, go back into the catheter through a first distal hole made in the side wall, go through the variable curvature section at least partially, come out through a second distal hole made in the side wall, go back into the catheter through the first proximal hole and close itself in a loop on the first fork passing through the constraint.

7. Catheter according to claim 6, wherein the second distal hole is positioned on the tip of the distal end of the catheter.

8. Catheter according to claim 6, wherein the second distal hole constitutes the aperture hole of said tip of the distal end of the catheter.

9. Catheter according to claim 6, wherein the first proximal hole is of such breadth as to prevent the crossing or transit of the constraint joined to the ascending branch.

10. Catheter according to claim 1, wherein the ascending branch goes through at least a first proximal hole in the side wall, so as to subtend the variable curvature portion, go back into the catheter through a first distal hole made in the side wall, go through the variable curvature section at least partially, come out through a second distal hole made in the side wall, go back into the catheter through a second proximal hole, different from the first proximal hole, and close itself in a loop on the first fork passing through the constraint.

11. Catheter according to claim 10, wherein the second distal hole is positioned on the tip of the distal end of the catheter.

12. Catheter according to claim 10, wherein the first and the second proximal holes are of such breadth as to prevent the crossing or transit of the constraint joined to the ascending branch.

13. Catheter according to claim 1, wherein the ascending branch and the descending branch of the traction wire respectively end with respective ends positioned on the proximal end of the catheter so as to permit their operation and pulling independently of each other.

14. Catheter according to claim 13, wherein the catheter, at said proximal end, comprises the traction wire having said respective ends so as to permit an independent and/or contemporaneous operation thereof so as to modify the curvature of the variable curvature section.

15. Catheter according to claim 1, comprising at least one guide element of an elongated and flexible shape, slidingly engageable inside the cavity or lumen of the catheter body, to come out through the tip which acts as a directing element of said catheter.

16. Catheter according to claim 1, comprising a stabilisation element of an elongated shape along a main direction of extension (X-X) and flexible, slidingly engageable inside the cavity or lumen of the catheter body which it is introduced in and from which it comes out through a stabilisation aperture positioned at the distal end of the catheter body.

17. Catheter according to claim 16, wherein said stabilisation element has a very slim and resistant diameter such as to permit the passage of operative guides and/or catheters while said stabilisation element is inserted inside the lumen.

* * * * *